United States Patent
Buttram et al.

[19]

[11] Patent Number: 6,125,706
[45] Date of Patent: Oct. 3, 2000

[54] HIGH TEMPERATURE ELECTROMAGNETIC ACOUSTIC TRANSDUCER

[76] Inventors: Jonathan D. Buttram, 714 College St., Bedford, Va. 24523; John H. Flora, 5108 Wedgewood Rd., Lynchburg, Va. 24503

[21] Appl. No.: 08/898,851

[22] Filed: Jul. 25, 1997

[51] Int. Cl.$^7$ .................................................. G01N 29/04
[52] U.S. Cl. .................................................. 73/643
[58] Field of Search .................. 73/643, 618, 620, 73/622, 587, 629, 779, 774; 324/228, 220, 219, 232, 240, 239; 62/259.2; 165/104.33; 361/699, 689, 688, 701

[56] References Cited

U.S. PATENT DOCUMENTS

| | | | |
|---|---|---|---|
| 4,100,809 | 7/1978 | Bobrov et al. | 73/638 |
| 4,184,374 | 1/1980 | Thompson et al. | 73/640 |
| 4,578,999 | 4/1986 | Abend et al. | 73/643 |
| 4,777,824 | 10/1988 | Alers et al. | 73/643 |
| 5,511,424 | 4/1996 | MacLauchlan et al. | 73/609 |
| 5,619,423 | 4/1997 | Scrantz | 364/507 |
| 5,689,070 | 11/1997 | Clark et al. | 73/643 |

*Primary Examiner*—Richard A. Moller
*Attorney, Agent, or Firm*—James W. Hiney

[57] ABSTRACT

An improved high temperature electromagnetic acoustic transducer (EMAT) for conducting inspections of materials with elevated temperatures, which has cooling means using gas cooling, such as air or nitrogen, for cooling the transducer RF coil, the onboard circuitry and magnets, while also providing for the easy removal of the coil and onboard circuitry. Prior art EMAT's are susceptible to failure since high temperatures reduces the signal quality of the electronics components, degrades the insulation of the RF coils, and permanent magnets can loose field strength.

17 Claims, 5 Drawing Sheets

HIGH TEMPERATURE ELECTROMAGNETIC ACOUSTIC TRANSDUCER

1.0 FIELD OF THE INVENTION

The present invention relates, overall, to electromagnetic acoustic transducers and, in particular to a design of an electromagnetic acoustic transducer that allows for use on materials of elevated temperatures.

2.0 DESCRIPTION OF THE PRIOR ART

Electromagnetic Acoustic Transducer (EMATs) are electrical devices that can transmit and receive ultrasonic sound waves in a conducting material without requiring contact of the probe with the material being inspected. An EMAT consists primarily of an electrical coil and permanent magnet or electromagnet. The electrical field produced by the coil introduces eddy currents in the conducting material when the coil is in close proximity to the material surface. When produced in the presence of a magnetic field, a Lorentz force results which is directly applied to the electrons. This force on the electrons is instantaneously transferred to the atoms that results in a stress wave in the material lattice. The ultrasonic wave produced by the EMAT is described mathematically as the cross product of the magnetic flux density ($B_o$) and induced eddy current density (J), thus;

$$F_L = J \times B_o$$

Therefore, the type of ultrasonic wave generated in the test material (longitudinal, shear, Rayleigh, lamb wave, etc.) is dependant upon the configuration of the magnet and coil used.

EMATs offer unique advantages when compared with piezoelectric transducers. An initial advantage is that no fluid couplant is required when using EMATs which eliminates the possibility of sensitivity losses and detection errors due to coupling variations. The ultrasonic sound waves are generated at and immediately below the surface of the material being tested, unlike conventional piezoelectric transducers where the sound is produced in the probe and transferred to the material through a coupling medium. Such a feature makes EMATs extremely useful where surface roughness or geometry prevents proper fluid coupling, or a surface temperature high enough to degrade or evaporate couplant material exists. In contrast, the EMAT coil(s) required for sound generation, do not touch the surface of the material and do not require the use of couplant. This eliminates changes that can occur in the beam characteristics (such as beam angle, beam shape & changes in time-of-flight) associated with the wear of the sound exit surface of a convenient contact transducer. It should be noted that EMATs commonly are used where the EMAT makes contact with the material but at points away from the location of sound production such as wear surfaces or rollers.

EMATs systems are used in increasing numbers primarily in the field of nondestructive examinations (NDE). One application is the inspection of high temperature piping such as that found in petrochemical and power plants. The temperatures of these components typically range from 750° F. to 1200° F. In both examples, wall thinning from corrosion or erosion can occur over time resulting in an unsafe condition. Since a fluid couplant cannot be maintained on materials at these temperatures, inspection using a piezoelectric transducer is not possible during operation. These inspections are limited to periods when the plant is shutdown. This can result in limited inspections due to the constraint of time and miles of insulated pipe that can exist in a typical petrochemical or chemical processing plant. In contrast, an EMAT, such as that described in the present invention, can be used during plant operation thus permitting continuous inspection of these type components.

3. SUMMARY OF THE INVENTION

An EMAT contains three critical components that are susceptible to failure due to high temperatures; onboard electronics, RF coil(s) and magnets. Electronic components typically cannot be operated at temperatures exceeding 150° F. without detrimental effects on signal quality. The RF coil must be very close to the material surface and can fail if the insulation between the windings of the coil degrades due to heat. Most permanent magnets experience a temporary loss in field strength when elevated to temperatures above 170° F. Permanent damage occurs at temperatures above 500° F. Electromagnets (DC or pulsed) produce heat when operating and must be kept cool or failure will occur due to electrical short circuit. The present invention provides a basic EMAT design that can operate when inspecting materials with surface temperatures up to 1200° F. without degradation of signal quality or internal components. This feature alone saves money as components need not be replaced as damage is rare.

It is an object of the present invention to provide a method to cool the EMAT coil, onboard circuitry and magnets using forced gas cooling such as air, nitrogen, etc.

It is another object of this invention to provide a magnet pole that can be efficiently cooled without interfering with the magnetic field produced by either permanent or electromagnets.

It is a further object of this invention to provide a coil design that can operate at high temperatures without degradation when used with the forced gas cooling system.

It is still another object of this invention to provide a high temperature EMAT design constructed of electronic sub-components (coil and PC card) that can be easily removed for repair.

A further object of this invention is to provide a high temperature EMAT design that is compatible for use with external attachments such as rollers for scanning and spring loaded legs for easy removal from insulation access holes.

These and other objects will become apparent when reference is had to the accompanying drawings.

4. BRIEF DESCRIPTION OF THE DRAWINGS

5. DESCRIPTION OF THE INVENTION

The present invention is an EMAT that can perform ultrasonic inspection of conducting materials with surface temperatures as high as 1200° F. Ultrasonic inspection includes determination of material thickness, defect detection, stress measurement and material property characterization.

Figure 1:
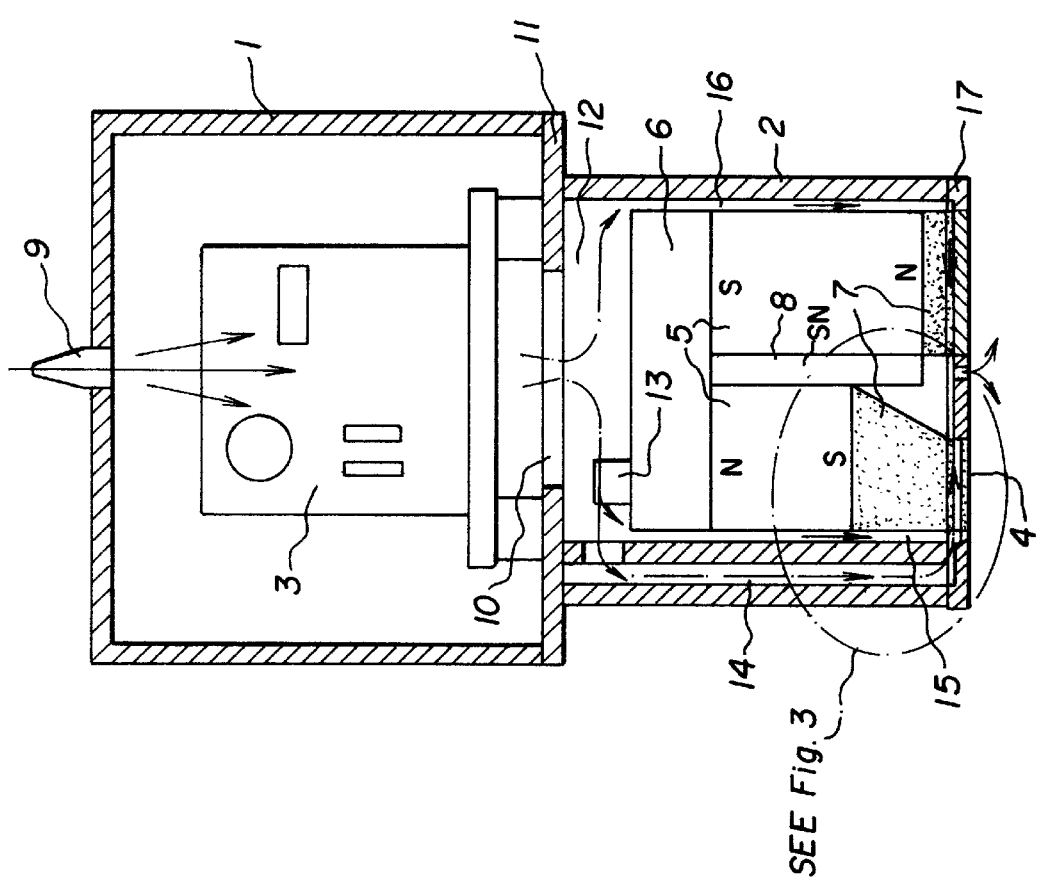
FIG. 1 is a cross-sectional view of the high temperature EMAT that illustrates the gas flow pattern required for cooling of the vital internal components.

FIG. 1 is a cross-sectional view of the high temperature EMAT. The EMAT consists of two sections; an upper housing 1 and lower housing 2, The upper housing contains onboard electronics 3 that provides impedance matching, signal amplification and frequency tuning circuitry. The lower housing contains the RF coil 4 and magnet assembly.

The magnet assembly is comprised of permanent magnets 5, flux return bar 6 and pole pieces 7. The flux return bar 6 mechanically supports the magnets as well as provides a path for the magnetic field to follow as it travels from one magnet to the other. The pole pieces 7 provide a magnetic path to the surface of the material being inspected, provide a means to extract heat away from the EMAT before reaching the temperature sensitive magnets, and concentrates the field when tapered to a smaller cross-sectional area. The pole pieces and flux return bar are made from an annealed steel material. The magnetic assembly is designed so that the magnetic field forms a loop traveling up one magnet, across the flux return bar, down the adjacent magnet into the material and back. A steering magnet 8 is used that forces the magnetic field into the material.

The EMAT is cooled using a nonflammable gas circulated through the housing. The gas first enters through the top lid of the EMAT 9 and flows directly over the onboard printed circuit card 3 containing all electronic components. After flowing past the electronic card(s) 3, the gas exits the upper housing and enters the lower housing through a large hole 10 located in the adaptor plate 11 which serves as the bottom to the upper housing as well as the top to the bottom housing. The gas flows into a distribution cavity 12 located at the top of the lower housing where a connector 13 for the coil wires is housed. The gas circulates around the connector and flows to both sides of the lower housing where three separate air passages are available, namely 14, 15, 16. Two air passages 15, 16 allow the gas to flow around the sides of the magnets providing direct cooling to these surfaces. Additional flow passages can be provided on the other sides of the magnet (not shown) if additional cooling is needed, although the primary flow should be on the EMAT ends as illustrated. A third passage 14 directs the gas flow through a wiring cavity which provide cooling to the coil wiring. The gas will flow through the three primary passages to the bottom of the lower housing and enter the coil plate 17.

Figure 2:
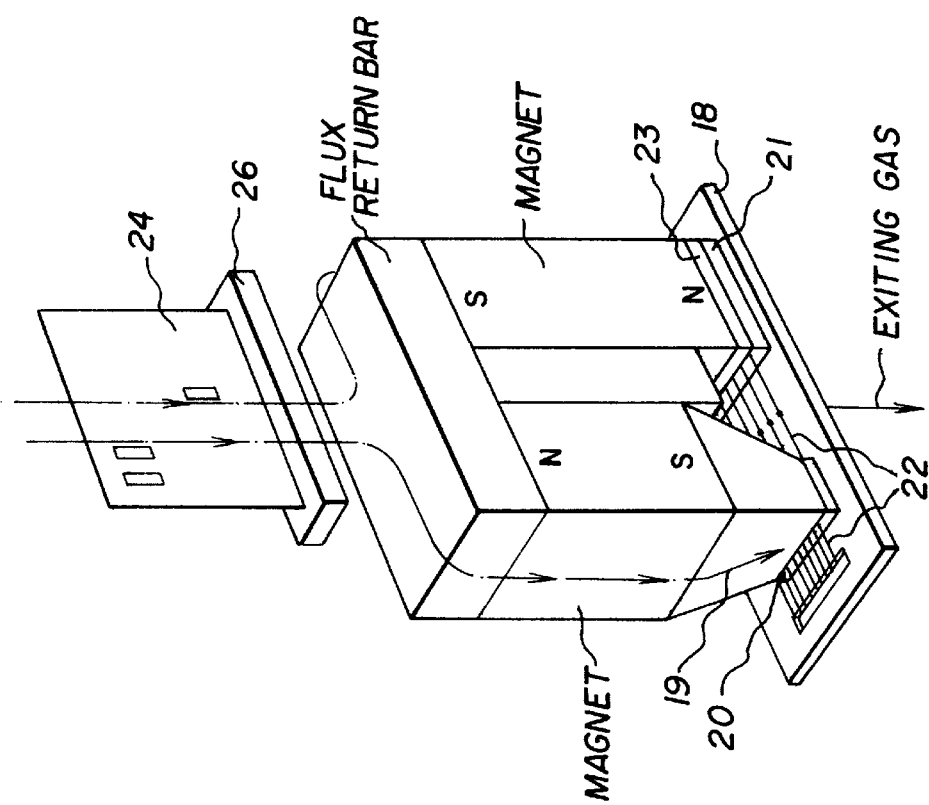
FIG. 2 is an isometric view of the EMAT internal components showing gas flow pattern.

FIG. 2 is an isometric view of the internal components of the EMAT. This drawing is provided to provide a view of the gas flow patterns without the obstructions of the EMAT case sides and top lid. The cooling gas flows around the electronic card 24 and connector 26, around the coil connector 27 down both ends of the magnet assembly, through cooling passages 22 and exits through small holes drilled in the coil plate The figure also illustrates the coil plate 18 and the four pole pieces that are required by this design. A tapered pole piece 19 is used to concentrate the magnetic field to its maximum flux density at the RF coil location. A mating pole piece 20 and a similar pole piece 21 both rest in a pocket in the coil plate and have small grooves machined in their surface that align with similar grooves 22 machined in the coil plate. A fourth pole piece 23 is provided as a mating surface to the lower pole 21. When assembled the machined grooves form passage ways in which cooling gases pass. Small machined filler parts are used to fill cavities around the pole pieces so that the gases are forced into the slots. FIG. 4 shows this area in greater detail as does FIG. 3.

Figure 3:
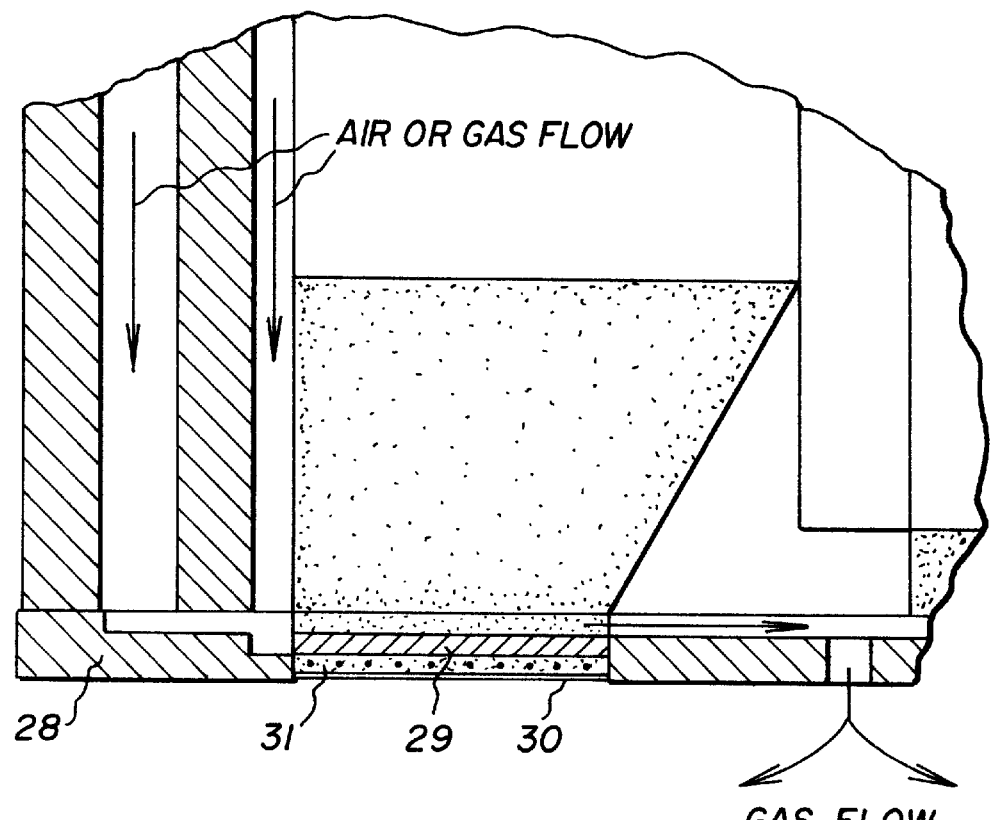
FIG. 3 is a side view of the bottom of the EMAT illustrating gas flow passages.

FIG. 3 is an expanded view of the bottom cross-section of the high temperature EMAT. This figure shows in more detail the air flow passages that are contained in the lower pole piece 29 and coil plate 28. Also shown is the RF coil assembly consisting of ceramic wear plate 30 and Teflon coated copper wire encapsulated in a ceramic potting compound 31.

Figure 4A:
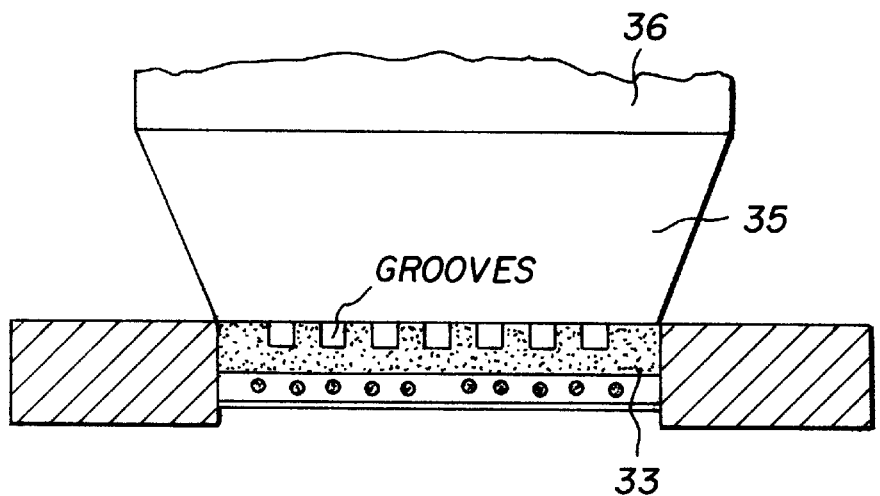
FIG. 4 illustrates two fabrication methods for the lower pole pieces; grooved design and drilled hole design.
Figure 4B:
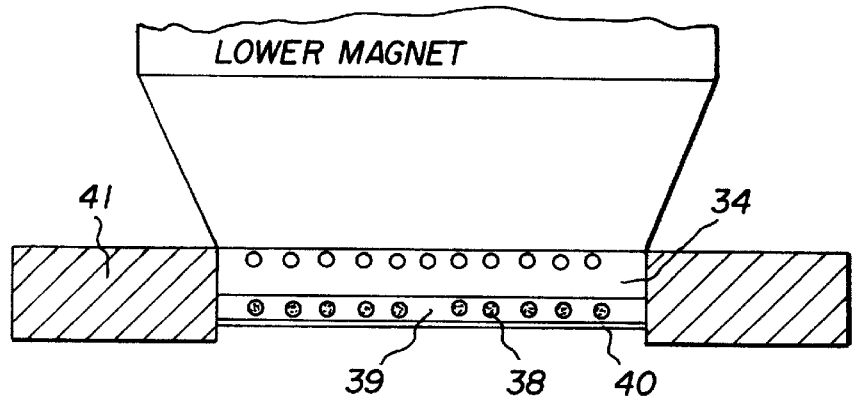

FIG. 4a)&b) are side views of a typical coil assembly with pole pieces. The lower pole 33 can either be fabricated using machined grooves which form rectangular channels when assembled with the upper pole piece 35, or by drilling small holes in the lower pole 34. When assembled, the holes or slots machined into the poles align with slots machined into the back side of the coil plate. The small flow channels located on the back of the coil plate and magnet pole holes, together provide a large surface area that extracts heat from both the coil plate and the lower magnet poles before reaching the temperature sensitive magnets. The size and number of flow passages contained in the coil plate and magnet poles determine the amount of heat that can be removed with a given gas flow. A thin layer of thermal insulation 37 can be used between the lower permanent magnet 36 and upper pole piece 35 to further protect the permanent magnet from excessive temperatures. The width of the slots used in the two pole piece configuration is kept at a minimum in order to minimize their effect on the magnetic field that is passed through the pole components and to maximize the velocity of gases which flows through the slots. The number and depth of the slots used is determined by the temperature of the material to be tested.

Although less costly to fabricate, the drilled hole design 34 is more limited since the size of the through drilled holes must be kept at a minimum to minimize the effect on the magnetic field. Therefore cooling efficiency cannot be increased without having some adverse effect on the magnetic field strength.

The RF coil assembly is designed to reduce heat input into the coil from the material surface while increasing heat extraction from the coil, from the pole component side or high temperature epoxy material. The coil 38 is manufactured using a standard Teflon coated magnet wire potted in a ceramic paste or high temperature epoxy acts as an electrical material 39. The ceramic paste acts as an electrical insulator between the individual coil windings preventing an electrical short at high temperatures. Located between the coil and the material surface is an additional layer of ceramic material 40 (alumina). This thin layer of alumina both insulates the coil from the heat generated by the hot surface and provides a tough wear surface that protects the coil from physical damage. The coil and ceramic wear surface are recessed a small amount up into the coil plate 41 in order to avoid direct contact of the coil area with the hot surface.

Figure 5:
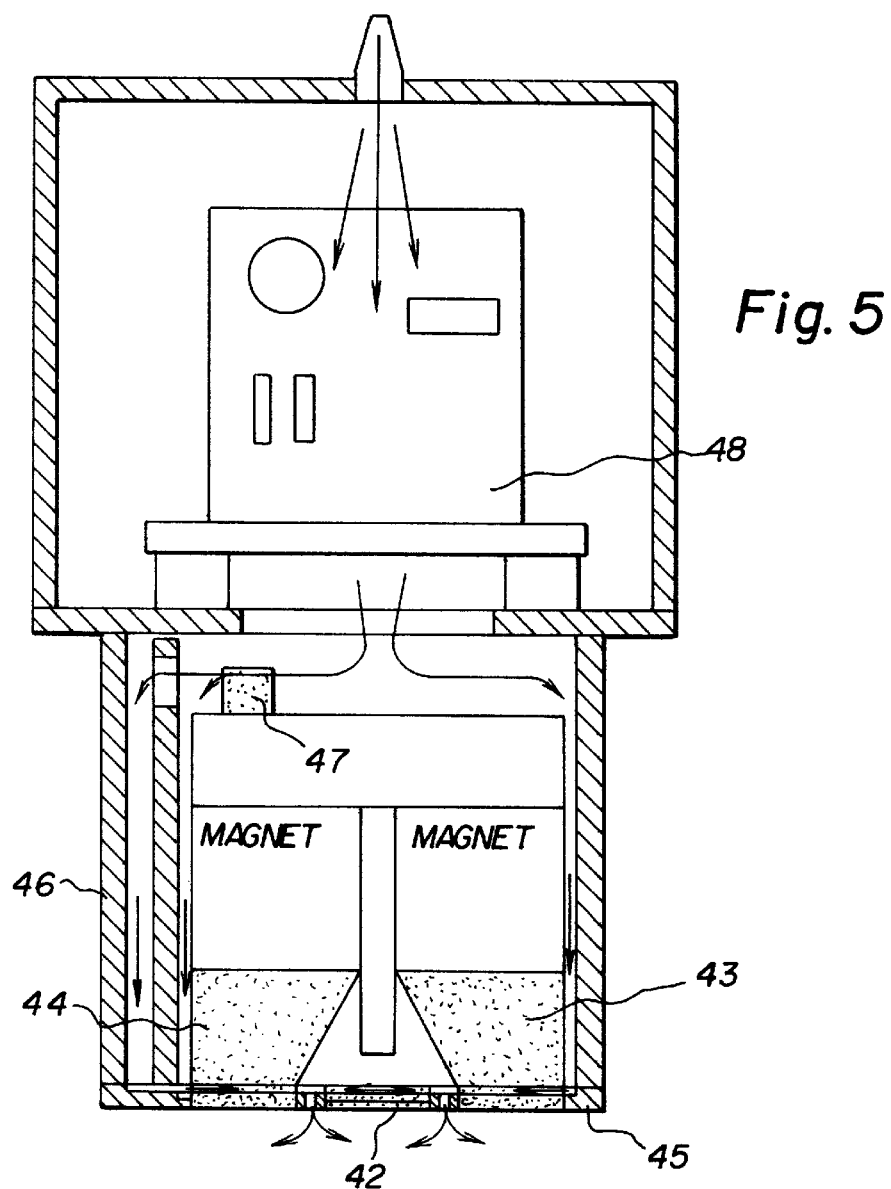
FIG. 5 is a cross-sectional view of the high temperature EMAT showing the air flow patterns associated with a coil positioned between magnet poles.

The cooling method used for the present invention is compatible for use with most magnet designs and coil configurations. The type of coil and position relative to the magnet poles will determine the type and direction of propagation of a wave mode. FIG. 1 illustrates a configuration where the coil 4 is placed underneath a pole (normal magnetic field). An alternate configuration is shown in FIG. 5 where the coil 42 is positioned between the pole pieces (tangential magnetic field). This design requires the use of two tapered upper pole pieces 43, 44 instead of only one, as shown in FIG. 1.

The present invention is modular in order to facilitate easy repairs during use. The coil plate 45 is designed so that it can be removed from the bottom of the EMAT. The wiring channel 46 can be removed exposing the coil connector 47 which can be disconnected for coil replacement. Also the PC card(s) 48, located in the EMAT housing are mounted using an edge connector and a slot machined into the lid of the upper housing. The PC card can be unplugged from the connector when the lid is removed.

Figure 6A:
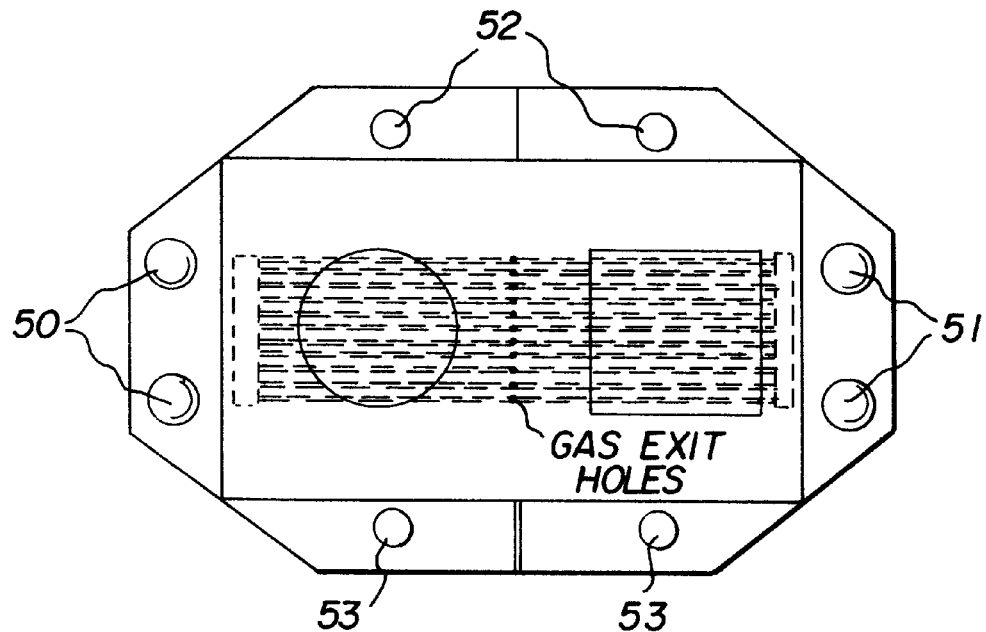
FIG. 6 is a bottom view of the high temperature EMAT showing cooling slot locations, ceramic wear surface, return path pole piece, roller attachment and spring loaded legs.
Figure 6B:
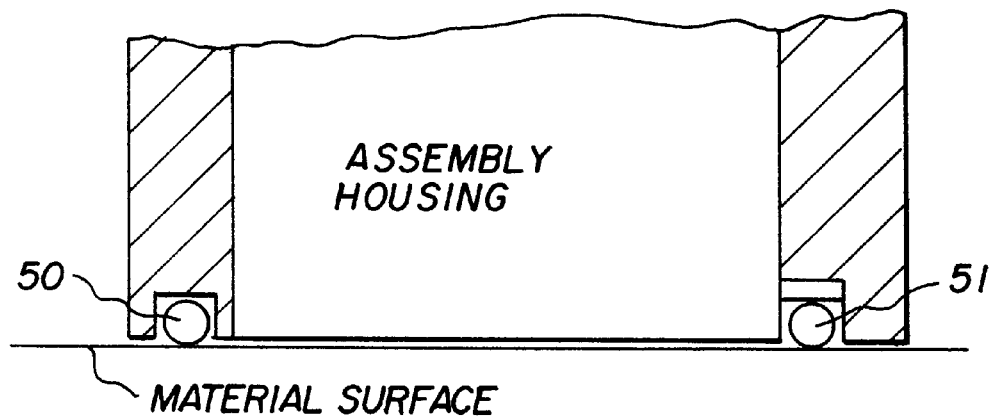
Figure 7:
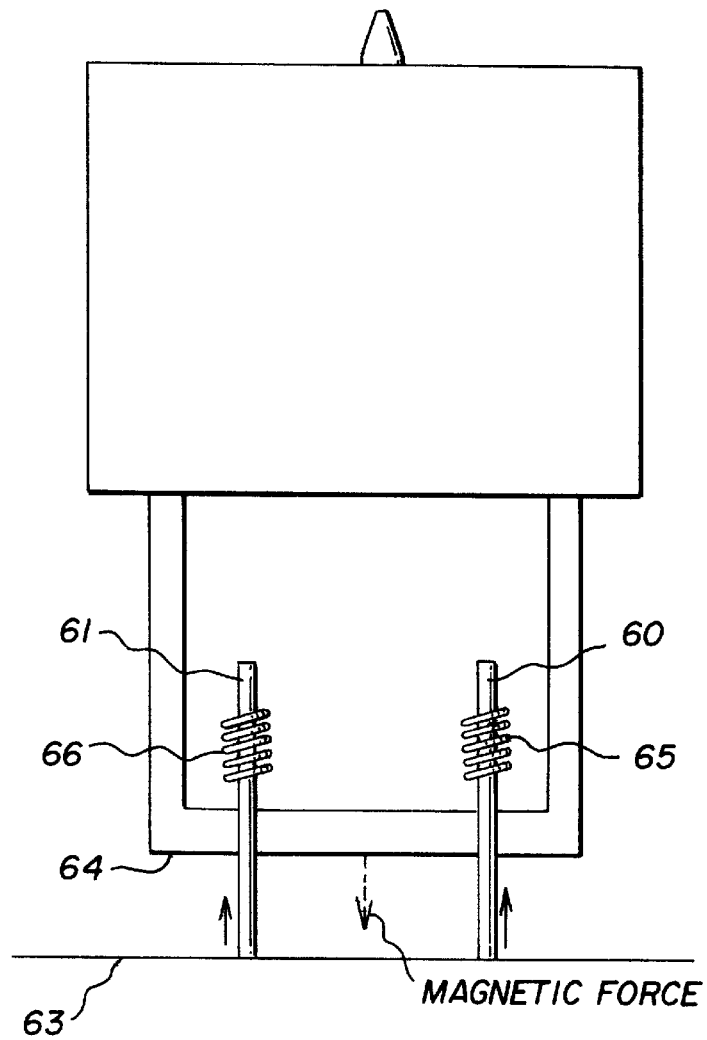
FIG. 7 is side view of the high temperature EMAT showing the spring loaded legs that are designed to provide a counter force to the magnetic attraction, thus helping in EMAT placement and removal, and, FIG. 8 is a block diagram of the electronics of the electronics of the EMAT.
Figure 8:
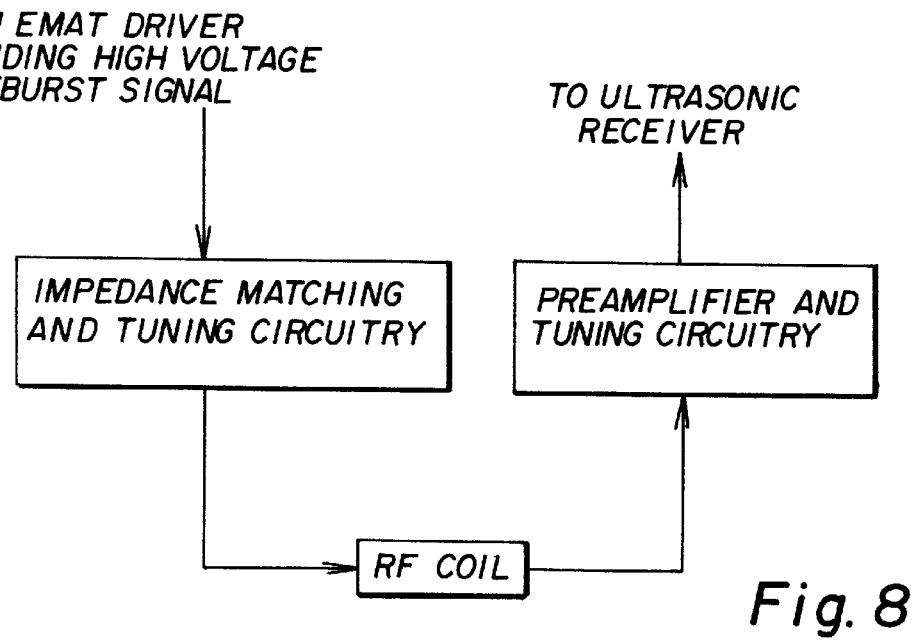

FIG. 6 is the bottom view of the high temperature EMAT. This view shows several features of this design. Rollers 50,51 can be attached to lower housing. Rollers 50 are necessary only when scanning of the EMAT is required. Without the rollers attached, the EMAT is held firmly on the surface of the material through magnetic attraction created by the magnets. The rollers are designed so that the bottom surface of the EMAT does not contact the material thus greatly reducing the resistance for lateral movement. Spring loaded legs 52,53 can be used to assist the operator in removing the EMAT from a magnet material. The spring loaded legs protrude beyond the bottom surface of the EMAT. As illustrated in FIG. 7, the legs 60,61 will engage with the surface 63 before the EMAT bottom 64 makes contact. The springs 65 & 66 create a force that counters the force which is produced by the magnets. This allows the EMAT to be placed on the material slowly and assists in its removal. The spring loaded legs are built so that they are a integrated part of the walls of the lower housing. This design requires that they lock in a depressed position to permit scanning.

Having described this invention and preferred embodiment there it will be obvious to those of ordinary still in the art that many changes and modifications can be made without departing from the scope of the appended claims.

We claim:

1. A high temperature electromagnetic acoustic transducer system having an RF coil for conducting inspections of materials for such purposes as material thickness, defect detection, stress measurement and material properties characterization among many, said system comprising
    a housing means for containing the components of said system, said housing designed to present the RF coil of said transducer system adjacent to but not in contact with the surface of the material being inspected,
    permanent magnet means located within said housing means to establish a magnetic field in the material being inspected,
    electronic means located within said housing to provide impedance matching, signal amplification and frequency tuning circuitry for adjusting and tuning said magnetic field,
    cooling means within said housing to cool said transducer during operation thereof whereby said system is able to withstand high operating temperature conditions from the material and/or the material environment being inspected as well as from its own operation.

2. A system as in claim 1 wherein said housing has rollers along one portion thereof for allowing lateral movement of said system along the material being inspected.

3. A system as in claim 1 wherein said housing has spring loaded legs which counter the attraction force applied by said transducer to thereby assist in placement and removal of said system.

4. A system as in claim 1 wherein said housing means comprises an upper section containing said electronic means and a lower section containing said permanent magnet means, said upper and lower sections are connected by a passage to allow for cooling of said system.

5. A system as in claim 4 wherein said cooling means comprises a non-flamable gas flow arrangement, said housing configured to allow said gas to flow through said upper section of said housing to cool the electronic means, through the lower section thereof to cool the volume between said permanent magnet means, RF coil and surface being inspected.

6. A system as in claim 5 wherein said housing means has gas flow channels in the sides thereof and passages in the portion facing the surface to be inspected and where said permanent magnet means is located in the middle of said housing to thereby allow for gaseous flow over said permanent magnet means and out onto said surface through said passageways.

7. A system as in claim 4 wherein said permanent magnet means includes upper and lower pole pieces permanent magnets and a flux return bar to allow for a solenoidal magnetic field which travels into the material being inspected and then back out into the permanent magnets.

8. A system as in claim 7 wherein there are two upper and lower pole pieces said permanent magnet means.

9. A system as in claim 7 wherein there are channels cut in a portion of said lower pole pieces to allow for gaseous flow through said pole piece to cool it during operation of said magnet means.

10. A system as in claim 8 wherein there are holes drilled in the lower pole pieces to allow for gaseous flow through said pole piece to cool it during operation of said magnet means.

11. A system as in claim 7 and including an RF coil assembly which contains coil windings embedded in a ceramic paste composition and/or high temperature epoxy to form the assembly.

12. A system as in claim 5 and including a layer of ceramic material on the base of the RF coil to insulate the coil assembly from the heat generated from the hot surface of the material being inspected and provides a physical barrier to the coil assembly itself.

13. A system as in claim 5 wherein said housing contains spring loaded legs which act to keep the system from contact with the surface of the material being tested and to allow it to be removed quickly.

14. A system as in claim 5 wherein said housing includes roller means to allow said system to be continuously moved laterally along the surface of the material being inspected while keeping said RF coil from contact with said surface.

15. A system as in claim 5 wherein said permanent magnet means includes an RF coil assembly, at least permanent magnet, a return flux bar and at least four pole pieces, said RF assembly being located within said pole piece whereby activation of said assembly causes stress waves in the material lattice.

16. A system as in claim 15 wherein there are at least two permanent magnets in said permanent magnet means and said return flux bar is in contact with both magnets.

17. A system as in claim 16 wherein at least one pole of said permanent magnets is tapered in cross-section.

* * * * *